(12) United States Patent
Kowallis

(10) Patent No.: US 6,916,447 B2
(45) Date of Patent: *Jul. 12, 2005

(54) APPARATUS AND METHOD FOR TRANSFERRING SMALL VOLUMES OF SUBSTANCES

(75) Inventor: Reid Burton Kowallis, Burlingame, CA (US)

(73) Assignee: Applera Corporation, Foster City, CA (US)

( * ) Notice: Subject to any disclaimer, the term of this patent is extended or adjusted under 35 U.S.C. 154(b) by 426 days.

This patent is subject to a terminal disclaimer.

(21) Appl. No.: 10/016,979

(22) Filed: Dec. 12, 2001

(65) Prior Publication Data

US 2002/0041829 A1 Apr. 11, 2002

Related U.S. Application Data

(60) Continuation of application No. 09/846,467, filed on Apr. 30, 2001, now Pat. No. 6,355,487, which is a division of application No. 09/293,659, filed on Apr. 16, 1999, now Pat. No. 6,245,297.

(51) Int. Cl.[7] .............................................. G01N 21/00
(52) U.S. Cl. ............................ 422/66; 422/63; 422/65; 422/67; 422/99; 422/100; 436/44; 436/46; 436/174; 436/180
(58) Field of Search .............................. 422/63, 65, 66, 422/67, 99, 100, 102, 104; 436/43, 44, 46, 50, 54, 174, 180

(56) References Cited

U.S. PATENT DOCUMENTS

| 3,164,304 A | 1/1965 | Jager et al. ................. 222/192 |
| 3,329,964 A | 7/1967 | Mutschler et al. ............ 346/78 |
| 3,334,354 A | 8/1967 | Mutschler .................. 346/140 |
| 3,850,775 A | 11/1974 | Bruneau et al. ............ 156/463 |

(Continued)

FOREIGN PATENT DOCUMENTS

| WO | WO 89/10192 | 11/1989 |
| WO | WO 94/00239 | 1/1994 |
| WO | WO 95/35505 | 12/1995 |
| WO | WO 97/44134 | 11/1997 |

OTHER PUBLICATIONS

Brussolo, J.S., and Dewitt, S.H., "Automated Sample Handling Systems," *NetSci Articles* 1(5):1–10 (1995).

(Continued)

*Primary Examiner*—Jill Warden
*Assistant Examiner*—Dwayne K Handy
(74) *Attorney, Agent, or Firm*—Jeffrey D. Frazier

(57) ABSTRACT

The present invention provides a method and apparatus for dispensing small volumes of selected substances, such as biological reagents or samples, onto substrates. According to one general embodiment, a plurality of spaced, tandemly-arranged substrates are advanced, e.g., by way of a conveyor, along a transport pathway extending over a reagent-supply location, such as a reservoir supported at a fixed position in a base. From a position over the reagent-supply location and the pathway, a reagent-transfer instrument, or tip, is extended along an axis through an intervening region, e.g., an opening defined by a surface of the conveyor, separating an adjacent pair of advancing substrates to contact reagent held at the reagent-supply location. The reagent-transfer instrument is then withdrawn, along with a portion of such reagent, through the intervening region to a position above the transport pathway. Once the conveyor has advanced a selected substrate, upstream of the intervening region, to a position aligned with the axis of the reagent-transfer instrument, a selected amount of reagent is transferred from the instrument onto a selected site of the substrate. Advantageously, the apparatus and method are readily adaptable for the production of micro-arrays having a great number of closely spaced spots.

11 Claims, 6 Drawing Sheets

U.S. PATENT DOCUMENTS

| | | | |
|---|---|---|---|
| 3,945,448 A | | 3/1976 | Sellers ........................ 177/25 |
| 4,057,145 A | * | 11/1977 | Wray et al. ................. 206/538 |
| 4,351,799 A | | 9/1982 | Gross et al. .................. 422/63 |
| 4,542,808 A | | 9/1985 | Lloyd, Jr. et al. ............. 186/56 |
| 4,681,742 A | | 7/1987 | Johnson et al. ............. 422/100 |
| 4,828,102 A | | 5/1989 | Dotson et al. .............. 198/588 |
| 4,893,513 A | | 1/1990 | Schroeder et al. ............ 73/827 |
| 4,952,518 A | | 8/1990 | Johnson et al. ............. 436/518 |
| 5,192,506 A | | 3/1993 | Kureshy et al. .............. 422/64 |
| 5,204,268 A | | 4/1993 | Matsumoto ................... 436/44 |
| 5,320,734 A | | 6/1994 | Yamasaki et al. ........... 204/415 |
| 5,389,408 A | | 2/1995 | DeVolk ....................... 427/559 |
| 5,425,918 A | | 6/1995 | Healey et al. ................ 422/64 |
| 5,443,791 A | | 8/1995 | Cathcart et al. .............. 422/65 |
| 5,508,200 A | | 4/1996 | Tiffany et al. ................ 436/44 |
| 5,525,515 A | | 6/1996 | Blattner ....................... 436/49 |
| 5,551,487 A | | 9/1996 | Gordon et al. ................. 141/1 |
| 5,587,522 A | | 12/1996 | Selby ........................ 73/54.28 |
| 5,595,707 A | | 1/1997 | Copeland et al. ............. 422/64 |
| 5,601,980 A | | 2/1997 | Gordon et al. ................. 435/6 |
| 5,639,665 A | | 6/1997 | Arai et al. .................... 436/50 |
| 5,733,509 A | | 3/1998 | Ackley et al. .............. 422/131 |
| 5,746,116 A | | 5/1998 | Smith .......................... 49/386 |
| 5,770,860 A | | 6/1998 | Franzen ..................... 250/288 |
| 5,807,522 A | | 9/1998 | Brown et al. ................. 422/50 |
| 5,811,306 A | | 9/1998 | Komatsu ..................... 436/54 |
| 6,156,575 A | * | 12/2000 | Fassbind et al. .............. 436/50 |
| 6,245,297 B1 | * | 6/2001 | Kowallis ..................... 422/66 |
| 6,251,686 B1 | * | 6/2001 | Studer et al. ............... 436/180 |
| 6,355,487 B2 | * | 3/2002 | Kowallis ..................... 436/44 |
| 6,458,582 B1 | * | 10/2002 | Kimura et al. ........... 435/286.2 |
| 6,696,302 B1 | * | 2/2004 | Franzen ..................... 436/180 |

OTHER PUBLICATIONS

Castellino, A.M., "When the Chips are Down," *Genome Research* 7:943–946 (1997).

Editorial, "Getting hip to the chip," *Nature Genetics* 18(3):195–197 (1998).

Haystack™ brochure, *The Automation Partnership*, First Edition:Oct. 1995.

Lemmo, A.V., et al., "Characterization of an Inkjet Chemical Microdispenser for Combinatorial Library Synthesis," *Analytical Chemistry* 69(4):543–551 (1997).

* cited by examiner

APPARATUS AND METHOD FOR TRANSFERRING SMALL VOLUMES OF SUBSTANCES

CROSS REFERENCE TO RELATED APPLICATIONS

The present application is a continuation of U.S. patent application Ser. No. 09/846,467, filed Apr. 30, 2001 now U.S. Pat. No. 6,355,487, which is a divisional application of U.S. patent application Ser. No. 09/293,659, filed Apr. 16, 1999, now issued as U.S. Pat. No. 6,245,297, which are incorporated herein by reference.

FIELD OF THE INVENTION

The present invention relates to the dispensing of substances, such as biological reagents and samples. More particularly, the invention provides an apparatus and method for transferring small volumes of substances onto one or more substrates.

BACKGROUND OF THE INVENTION

As the sensitivity of analytical techniques continues to improve, it is increasingly desirable to carry out chemical and biochemical assays using very small volumes of samples/reagents. This is especially true in situations involving expensive substances. Accordingly, it is now popular to utilize very small volumes of such substances laid down as "spots" on the surface of a substrate, such as a slide, micro-card, chip or membrane.

Not only is it often desirable to provide ultra-small volumes of individual samples and/or reagents in the form of spots, it is becoming increasingly popular to arrange numerous such spots in close proximity to one another in the form of an array on a substrate. For example, a lab technician might need to evaluate a specimen for the presence of a wide assortment of target biological and/or chemical compounds, or to determine the reaction of many different specimens against one or more reagents, such as labeled probes. High-density array formats, or "microarrays," permit many reactions to be carried out in a highly parallel fashion, saving space, time and money.

A variety of methods are currently available for making microarrays. Microarrays can be made, for example, by a robotic arm device having a spotting tip that moves successively between a sample-pickup well in a sample array, e.g., a microtitre plate, and a selected array position. Although high-density arrays of selected substances can be constructed by this approach, the production time and efficiency is limited by the fact that the regions of the microarray (or microarrays, if several are being constructed at once) are deposited one-by-one in a serial fashion. Additional time and effort is required where a plurality of different substances are laid down in the array, as the spotting tip must be cleaned and dried prior to being used with each new substance.

Multi-channel micropipette devices are available for laying down several reagent spots at once. Devices of this type typically have 8 or 12 micropipettes, fixed side-by-side in a linear array. Generally, these devices are unsuitable for quickly producing very dense arrays, as the size of each micropipette and any associated service connections (e.g., supply tubing, electrical connections, etc.) limits the minimal center-to-center spacing (pitch) that can be achieved for adjacent spots. Also, since only a few spots (usually 8 or 12) can be laid down at a time with such devices, the production of very dense arrays, e.g., having hundreds or thousands of spots with a submillimeter pitch, tends to be a very tedious and time-consuming process.

Another technique employs an array of pins arranged to simultaneously dip into an array of reservoirs, e.g., the 96 wells of a microtitre plate, to pick up one or more selected substances for transfer to a substrate, such as a membrane. Similar to the multi-channel pipette devices, the pitch spacing is limited by the size of each pin. Also, the pins of such arrays are typically arranged to match the pitch of a conventional supply-well array, typically 2¼, 4½, or 9 mm center-to-center. Thus, similar to the multi-channel pipetters, the production of very dense arrays can only be accomplished by sequentially laying down a number of sub-arrays, e.g., in a staggered or interleaved fashion—a very cumbersome and inefficient endeavor.

As an additional disadvantage, most of the known spotting techniques require the handling or transfer of substances between multiple receptacles (e.g., pipettes, flasks, vials, etc.) and/or flow lines (e.g., channels, hoses, tubing). Such transfers frequently result in a loss or contamination of the substance, thereby reducing the overall efficiency and sensitivity of the assay. Particularly with regard to expensive substances, it is generally desirable to keep such losses to a minimum.

In view of the above, the need is apparent for a device and method useful for delivering a micro-volume of a substance onto a substrate in a quick and efficient manner. Preferably, the device should be relatively easy to use, cost effective and readily adaptable for the production of micro-arrays having a great number of individual spots.

SUMMARY OF THE INVENTION

In one of its aspects, the present invention provides an apparatus for spotting a selected substance (e.g., a liquid sample or reagent, or micro-particles such as beads) onto one or more substrates.

In one general embodiment, the apparatus of the invention includes a base, adapted to held one or more reagents, and a conveyor. The conveyor includes a movable surface defining (i) a plurality of spaced, tandemly-arranged substrate-support regions, each of which is adapted to support a substrate, and (ii) an opening between each adjacent pair of substrate-support regions. The conveyor is operable to advance the substrate-support regions along a transport pathway extending over the base. Further included is a transfer instrument or head having a spotting tip mounted for movement along an axis, toward and away from a raised position at which the tip is disposed above the conveyor surface. Shifting means, e.g., an actuator (such as a solenoid, or the like), are operatively connected to the tip for moving the same along its axis. A control unit is operatively connected to the conveyor and the actuator. At the direction of the control unit, a selected opening of the conveyor surface can be advanced to a position generally aligned with the axis of the transfer tip, at which point the control unit can signal the shifting means to shift the tip away from its raised position through such opening to contact reagent in the base. The shifting means can then withdraw the tip from the reagent and through the opening by shifting the tip toward its raised position. A selected site of a substrate-support region upstream of the selected opening can then be advanced to a position generally aligned with the axis of the transfer tip, at which point the control unit can signal the shifting means to shift the tip away from its raised position toward such site to transfer a selected amount of reagent from the tip to a selected region of a substrate at the substrate-support region.

According to one embodiment, one or more additional transfer heads and associated shifting means are disposed at spaced positions along the transport pathway, and structure is provided in the base for holding one or more reagents at each of the spaced positions. Such structure can include, for example, one or more tube holders (e.g., apertures or bores formed along a top surface of the base). The various transfer heads can be positioned along a line running parallel with the transport pathway, or one or more of the transfer heads can be laterally offset from the other transfer heads.

In one embodiment, a plurality of transfer heads are disposed in a row extending laterally or obliquely across the conveyor surface at one or more of the spaced positions along the transport pathway.

One embodiment contemplates a channel or cavity extending through at least a portion of the base. For example, an elongate channel can extend longitudinally through a central region the base. Optionally, a flow line can communicate a remote fluid source with the channel. In one such arrangement, a fluid flow line is connected to a fitting at one end of the channel. An outlet of the flow line is arranged so as to direct a selected fluid, passed through the line, into and along the channel. The channel can further include an egression port, e.g., at a distal end, through which any fluid(s) directed into the channel can exit.

In one embodiment, the base of the apparatus is adapted to hold one or more reagent reservoirs (e.g., tubes, vials, or the like) such that a lower region of each reservoir extends at least partially into a channel of the base, such as the channel just described. For example, apertures can be formed along the top of the base into which respective reagent-holding tubes can be inserted. Each aperture, in this exemplary construction, communicates the interior of the channel with a region between the base and the transport pathway. With the tubes in place along the base, a cooling fluid (e.g., a gas, or water) passed through the channel can impinge upon the accessible external surfaces of the tubes, thereby cooling the tubes so as to discourage evaporation of the reagent(s) held therein.

According to one exemplary design, the transfer tip, when shifted away from its raised position, with its axis of motion unobstructed (i.e., through an opening defined by the conveyor surface), is adapted to enter at least partially into a channel extending through the base. At this position, a cleaning fluid (e.g., a liquid solvent) passed through the channel can clean the tip. Optionally, a dry, warm gas subsequently passed through the channel can be used to dry the cleaned tip.

Any suitable transfer instrument or head can be used, including contact and/or non-contact type devices. For example, the apparatus can employ a transfer head having an elongated tip in the nature of a pin or rod. In a typical construction, a relatively narrow rod is employed, e.g., one having a distal end less than about 500 $\mu$m in diameter, and preferably less than about 250 $\mu$m in diameter. In another exemplary arrangement the tip includes a channel of capillary size (e.g., less than about 1 mm in diameter) adapted to draw in a liquid reagent, when shifted into contact therewith, by way of capillary action. Still further embodiments contemplate the use of a micropipette, syringe device, jetting apparatus, or other "sip and spit" assembly, as the transfer tip.

Preferably, the transfer tips of the transfer head or instrument are of an independent construction. The tips are not permanently fixed spatially with respect to one another. Each individual transfer tip can be attached to and detached from the head, without affecting or otherwise disturbing any other transfer tip(s) of the apparatus.

One embodiment of the invention teaches a transfer head having a plurality of spotting tips mounted side-by-side, in spaced relation. Each tip, in this embodiment, is adapted for movement along a respective axis, toward and away from a raised position at which the tip is disposed above the conveyor surface.

The conveyor of the transfer apparatus can be, for example, a linear-type conveyor or a carousel-type arrangement, among others. In one embodiment, the conveyor surface takes the form of an elongate web. Each of the substrate-support portions of the web, in this embodiment, defines a substrate portion or region that can be spotted. That is, the web and substrates are of an integral construction. In one particular arrangement, the web material is a flexible, membrane material. In another embodiment, the conveyor surface takes the form of an elongate flexible belt, e.g., a rubber or metallic endless belt, upon which separately formed substrates (e.g., 1"×3" micro-cards) can be removably placed. In one particular arrangement, the belt includes a pocket at each of its substrate-support regions for receiving respective micro-cards and maintaining the position of each at a known location as it is advanced along the transport pathway and spotted.

Another general embodiment of the spotting apparatus, as taught herein, includes a conveyor belt comprising a plurality of substrate-support regions separated from one another by intervening open regions therebetween. A base is located beneath the conveyor belt for supporting one or more reagent reservoirs (e.g., tubes, vials, or the like). A transfer instrument or head is disposed above the base and the conveyor belt, having a spotting tip mounted for movement between (1) a raised position above the conveyor belt, (2) a reagent dispensing position for depositing reagent on a substrate carried by one of the substrate-support regions, and (3) an extended position below the conveyor belt which is achieved by passing the tip through one of the open regions. Further included are means for moving the conveyor belt (including, for example, a motor, drive train, and driven roller) along a transport pathway such that the substrate-support regions pass generally along a plane extending between the base and the transfer head. Shifting means (e.g., an actuator, such as a z-motion actuator) are operatively connected to the spotting tip for shifting it between the extended, reagent dispensing, and raised positions. One or more controllers are operatively connected to the moving means and shifting means, the controllers being operable to (i) shift the spotting tip from its raised position to its extended position by traversing a selected open region in the conveyor belt, for withdrawing reagent from a reservoir supported by the base, (ii) raise the spotting tip after step (i) to a position above the conveyor belt, (iii) move the conveyor belt so that a selected substrate is positioned below the raised spotting tip, (iv) move the spotting tip to a reagent dispensing position so that reagent is deposited onto a selected region of the selected substrate, (v) after reagent deposition, raise the spotting tip to its raised position, (vi) move the conveyor belt so that the spotting tip is positioned above another open region. If desired, the controller can repeat steps (i)–(vi) a selected number of times.

A further general embodiment of a spotting apparatus, as taught herein, includes a base, adapted to hold a reagent, and a conveyor. The conveyor includes a surface defining (i) a plurality of spaced, tandemly-arranged substrate regions, and (ii) an opening between adjacent substrate regions. The conveyor is operable to advance such regions along a transport pathway extending over the base. A transfer instrument or head is provided, having a spotting tip mounted for movement along an axis, toward and away from a raised position at which the tip is disposed above the conveyor surface. Shifting means, e.g., an actuator, are operatively connected to the tip for moving the same along its axis. A control unit is operatively connected to the conveyor and the shifting means. At the direction of the control unit, a selected opening of the conveyor surface can be advanced to a position generally aligned with the axis of the transfer tip, at which point the control unit can signal the shifting means to shift the tip away from its raised position through such opening to contact reagent in the base. The shifting means can then withdraw the tip from the reagent and through the opening by shifting the tip toward its raised position. A selected site of a substrate region, upstream of the selected opening, can then be advanced to a position generally aligned with the axis of the transfer tip, at which point the control unit can signal the shifting means to shift the tip away from its raised position toward such site to transfer a selected amount of reagent from the tip thereto.

In one particular arrangement of the spotting apparatus, the conveyor surface is a flexible web material, such as a membrane or the like.

In another of its aspects, the present invention provides a method for spotting a selected substance (or substances) onto one or more substrates.

According to one general embodiment, the method includes the steps of:

(i) advancing a plurality of spaced, tandemly-arranged substrates along a transport pathway extending over a reagent-supply location;

(ii) from a position over the reagent-supply location and the pathway, (a) extending a reagent-transfer instrument, or tip, through an intervening region separating an adjacent pair of advancing substrates to contact reagent held at the reagent-supply location, (b) withdrawing the reagent-transfer instrument, along with a portion of such reagent, through the intervening region to a position above the transport pathway, and (c) transferring a selected amount of reagent from the reagent-transfer instrument onto a selected region of a selected substrate upstream of the intervening region.

In one embodiment, the substrates are integrally formed as spaced-apart expansive portions provided along an elongate web of material (e.g., a membrane material), and each of the intervening regions is an opening formed through the web of material (e.g., a cut-out region) between adjacent substrate portions.

In another embodiment, the substrates are advanced using a conveyor having a belt (e.g., a flexible endless belt) with a plurality of tandemly-arranged substrate-support regions. Each of the substrates, in this embodiment, is placed at a respective one of the substrate-support regions.

According to one embodiment, the transport pathway extends over a plurality of reagent-supply locations, disposed at spaced positions along the pathway. Step (ii), in this embodiment, is performed at two or more of the spaced positions in a fashion effective to produce a plurality of reagent spots on the selected substrate. The reagent spots can be placed along a line extending substantially parallel to the transport pathway, and/or one or more of the reagent spots can be placed at positions that are laterally offset from the other reagent spots.

In one embodiment, step (ii) is performed at least twice, in a substantially parallel fashion, using separate reagent-transfer instruments at one or more of the spaced positions.

Another embodiment contemplates the additional steps of: removing any reagent(s) being held at the reagent-supply location(s); extending at least a portion of each reagent-transfer instrument into a respective reagent-supply location; and flowing a cleaning fluid (e.g., a liquid solvent) along the reagent-supply location so that it contacts and cleans each reagent-transfer instrument or tip. Optionally, a drying fluid (e.g., a warm, dry gas) can be passed along the reagent-supply location, subsequent to such cleaning step, such that it contacts and dries each transfer instrument.

In one embodiment, one or more reagent reservoirs, or vessels, are placed at respective reagent-supply locations; and a cooling fluid is passed along the reagent-supply location so that it contacts the vessel, thereby reducing evaporative loss of any liquid reagent held therein.

A further embodiment contemplates, prior to step (i), the additional step of retrieving a vessel containing a selected reagent from a storage location, and placing the vessel at a reagent-supply location; and, subsequent to step (ii), the step of retrieving the vessel from the reagent-supply location, and returning the vessel to its storage location. In this way, the use of intermediate vessels, and consequent loss of reagent, is avoided.

Still a further aspect of the invention provides a substrate, bearing one or more reagent spots (e.g., a micro-array), produced in accordance with the method taught herein.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which.

DETAILED DESCRIPTION OF THE INVENTION

The following discussion of the preferred embodiments of the present invention is merely exemplary in nature. Accordingly, this discussion is in no way intended to limit the scope of the invention.

One aspect of the invention provides an apparatus for transferring a selected substance or substances, such as biological reagents and/or samples, onto one or more substrates. In one general embodiment, the apparatus includes a base adapted to hold a supply of reagent, e.g., in a reservoir. Means are provided for moving a plurality of tandemly-arranged substrates, separated from one another by intervening open regions, along a transport pathway extending over the base. A reagent-transfer instrument is mounted for movement toward and away from a raised position at which a transfer tip, along one end of the instrument, is disposed above the transport pathway. Shifting means are provided for moving the transfer tip along an axis, toward and away from its raised position. A control unit is operative to (i) shift the transfer tip away from its raised position through a selected open region to contact reagent held at the reagent-supply location, (ii) withdraw the tip, along with a portion of such reagent, through the open region to a position above the transport pathway, and (iii) to shift the tip away from its raised position toward a selected substrate upstream of the selected open region, to transfer a selected amount of reagent from the tip to a selected region of the selected substrate.

Figure 1:
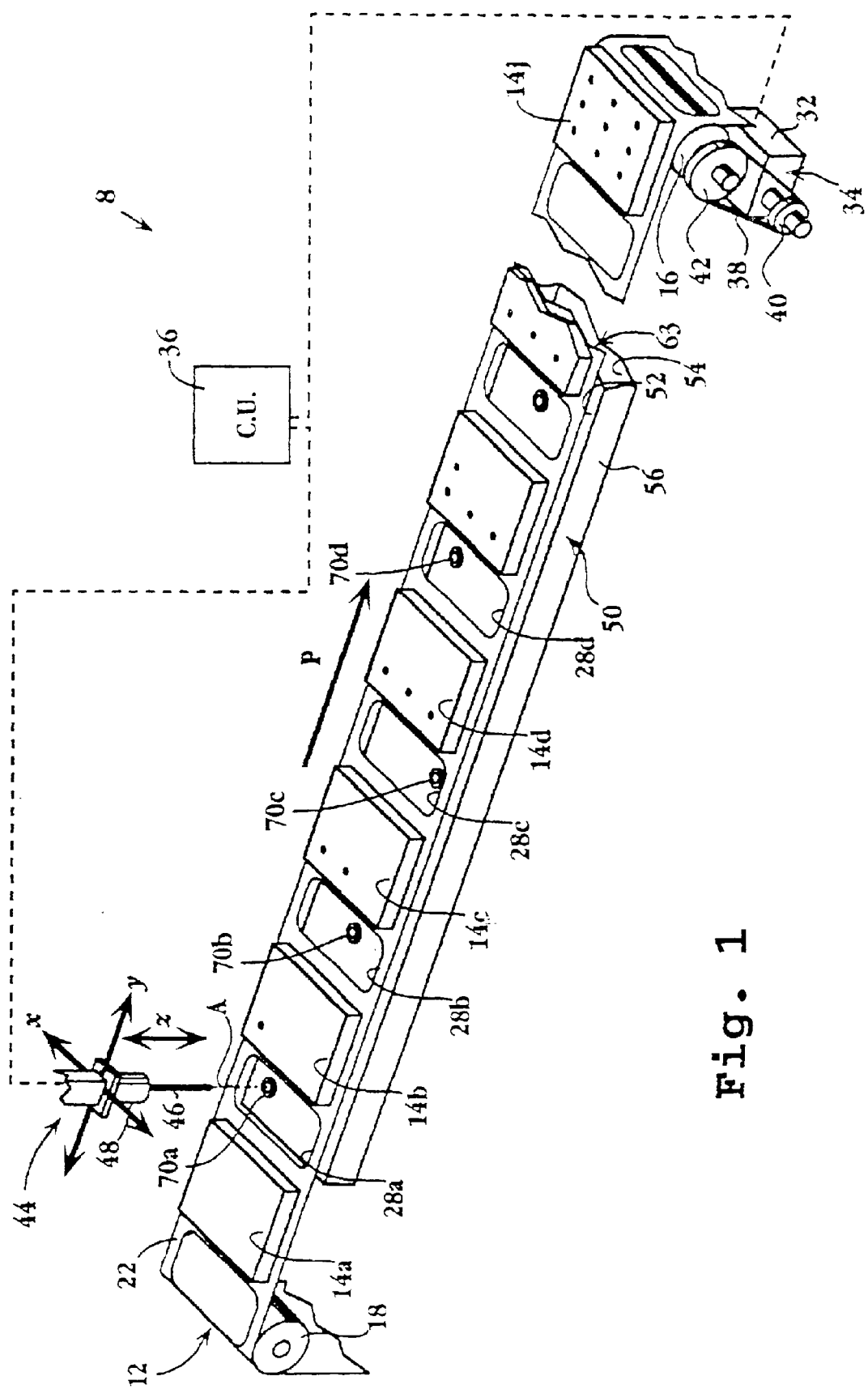
FIG. 1 is a partially schematic, perspective view of a reagent-transfer apparatus, along with several exemplary substrates, according to the teachings of the present invention.

An exemplary arrangement of a reagent-transfer apparatus, as provided by the present invention, is indicated generally by the reference numeral 8 in FIG. 1. In this embodiment, a conveyor, denoted generally as 12, is adapted to move a plurality of tandemly-arranged substrates, such as 14a–14d, separated from one another by intervening open regions, as at 28a–28c, along a transport pathway, "P," that extends over a base 50. Conveyor 12 includes a driven roller 16 at one of its ends, and an idler roller 18 at its other end. A flexible belt, denoted as 22, extends over the driven and idler rollers. Optionally, conventional support rollers (not shown) can be provided between the drive and idler rollers, and any known slack adjusting mechanism (not shown) can by used to maintain a desired tension in the belt.

Any suitable flexible belt can be used for supporting and transporting the substrates. In one embodiment, the conveyor belt is formed of a flexible polymer material, e.g., rubber or the like. In another embodiment, a flexible metal belt, such as a steel band, is utilized. While the particular material composition of the belt is not critical, it is important that the belt includes at least one region configured to support a substrate, and an opening downstream of the substrate-support region. For example, in the present embodiment, belt 22 includes (i) a plurality of substrate-support regions, such as 26a–26d (FIG. 2), and (ii) an opening, as at 28a–28c, between adjacent substrate-support regions.

Although not visible in the figures, the conveyor belt can further include features for locating and maintaining each substrate at a desired position and orientation thereon. For example, a sunken region or pocket can be formed at each substrate-support region of the conveyor belt, dimensioned to closely fit the outer dimensions of a given type of substrate, e.g., a 1"×3" micro-card.

A motor, as at 32 in FIG. 1, is provided for advancing conveyor 12. Motor 32 can be of any suitable, known type. Preferably motor 32 is a stepper motor, though other motors can be used, e.g., servos, etc. Motor 32 is operatively connected to a drive train, denoted generally as 34, for driving the conveyor in accordance with the commands of a control unit, as indicated schematically at 36. Any suitable drive train can be employed. In the illustrated arrangement, an endless chain or belt 38 couples a drive sprocket 40 affixed to an output shaft of motor 32 with a driven sprocket 42 of roller 16. As will be discussed, the drive may be intermittent or continuous.

Figure 2:
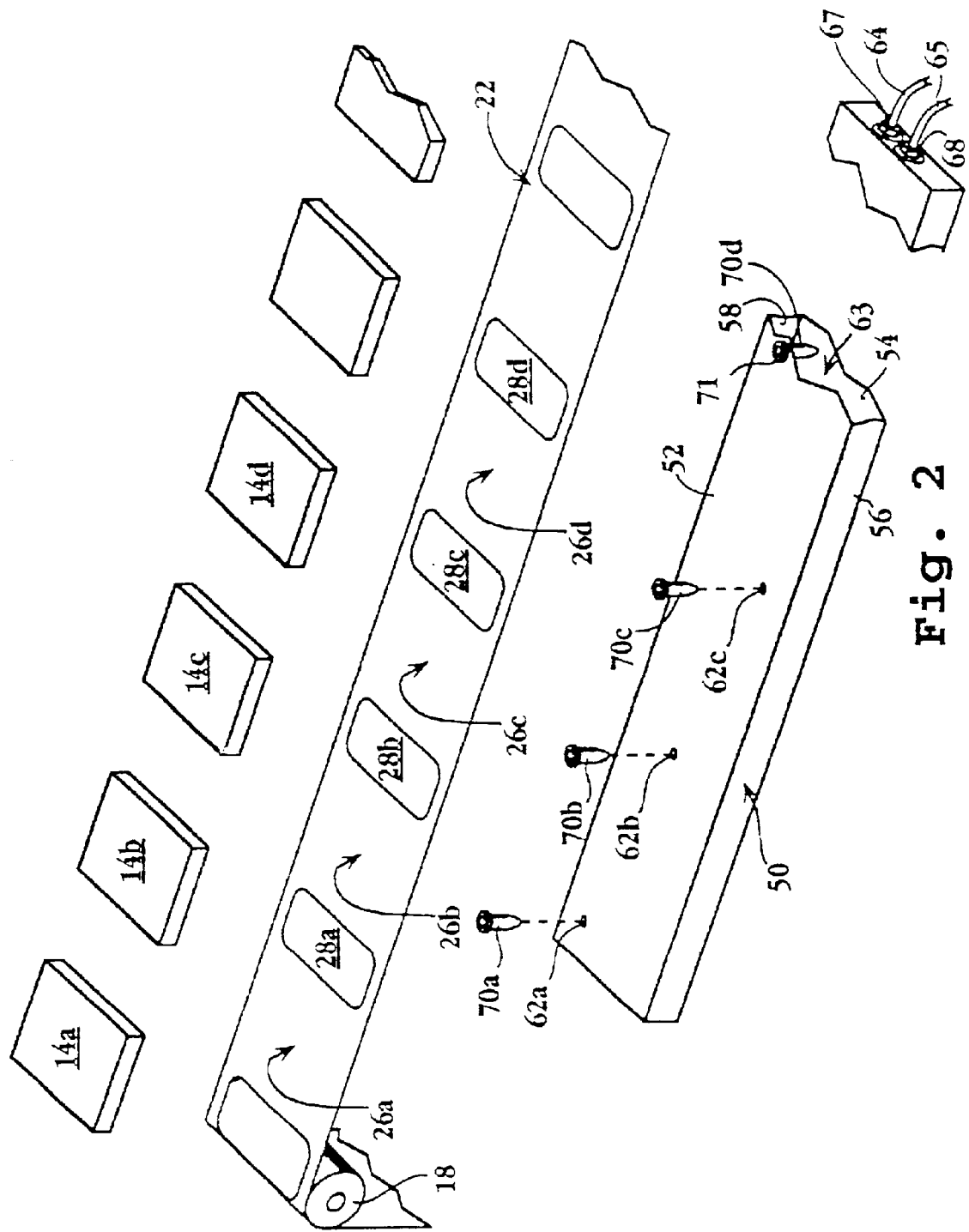
FIG. 2 is a partial exploded view of the apparatus and substrates shown in FIG. 1.
Figure 3:
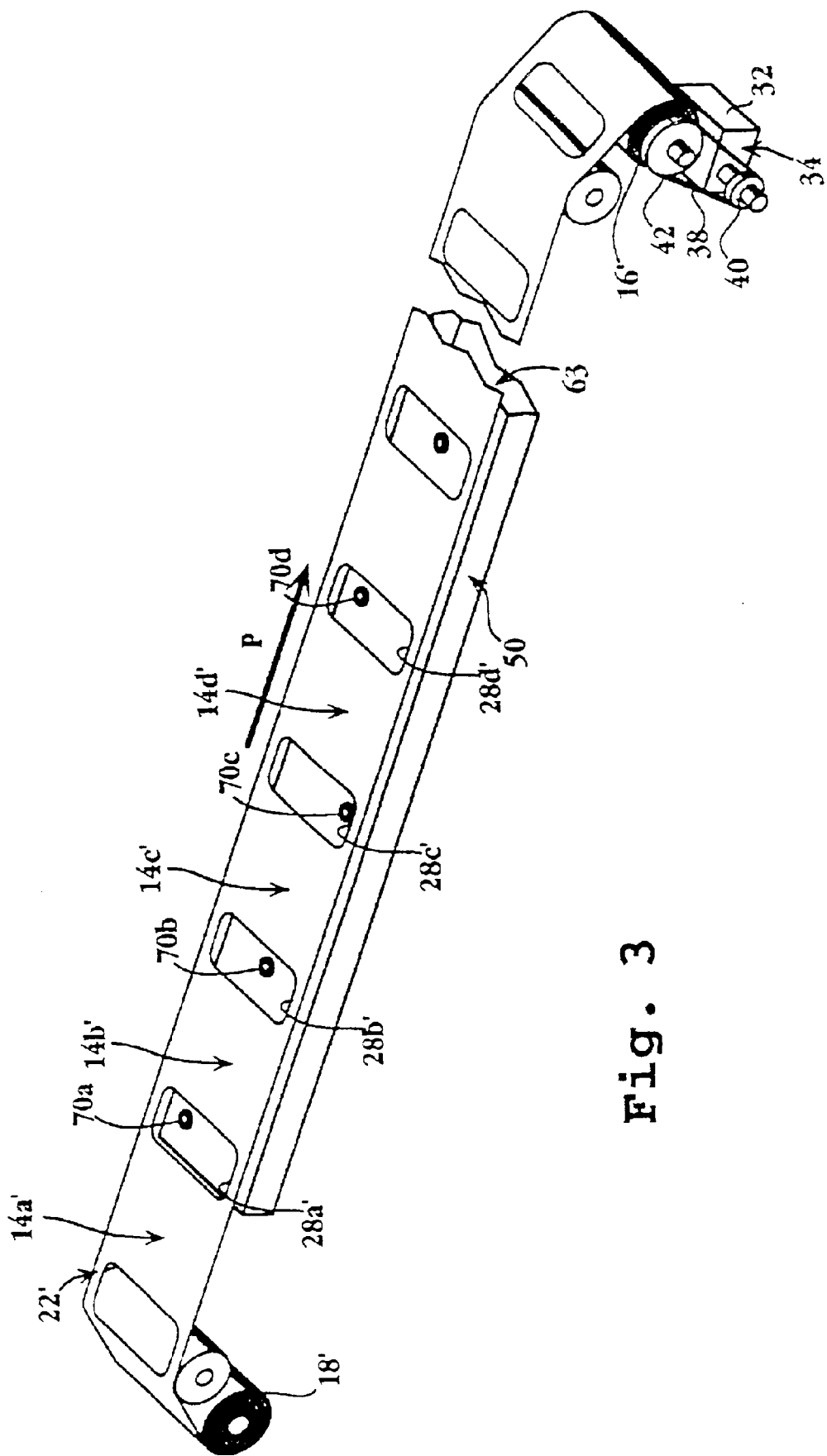
FIG. 3 is a perspective view of another embodiment of a reagent-transfer apparatus, according to the present invention.

Instead of placing a plurality of separately formed substrates on the conveyor belt, as shown in FIGS. 1 and 2, the belt itself can provide a plurality of substrates. That is, the belt and substrates can be of an integral construction—e.g., with each substrate-support region, itself, defining a substrate. In the exemplary arrangement of FIG. 3, a web 22' of a flexible material (e.g., a membrane) extends from a supply roll 18', over base 50, to a driven take-up roll 16'. Web 22', in this embodiment, includes a plurality of tandemly arranged substrate portions, such as at 14a'–14d', each defined by an expansive region of the belt. Each adjacent pair of substrate portions of the web, in this embodiment, are separated from one another by intervening open regions in the nature of apertures or holes, as at 28a'–28c', defined by web 22'. Upon driving take-up roll 16' in a clockwise direction, the substrate portions are moved along transport pathway P, over base 50. From the take-up roll, the substrate portions can be subjected to further processing (e.g., severing the various substrate portions into separate, individual sheets), if desired.

Returning now to FIG. 1, a reagent-transfer instrument or head, as at 44, is mounted for movement over the transport pathway P. In the illustrated arrangement, transfer head 44 includes a transfer tip 46 movable along an axis, denoted as "A." Particularly, tip 46 is adapted for movement toward and away from a raised position at which it is disposed above the transport pathway P.

The type of transfer tip utilized is not critical, provided only that it is capable of picking up a selected reagent from a reservoir and transferring the reagent to a selected substrate. The particular type of transfer tip used will often be determined, at least in part, by the nature of the reagent employed and the desired spot size (e.g., volume) to be formed on each substrate. Exemplary tips useful for the transfer of liquid reagents include pins, rods, quills, syringes, pipettes, jetting devices (e.g., "sip and spit" devices), among others. Exemplary tips useful for transferring solid or semi-solid reagents, such as micro-beads, include electrostatic and/or magnetic pins or rods, as well as vacuum capillary tubes, and the like. While only one transfer tip is shown on the head in FIG. 1, other embodiments contemplate multiple tips (2 or more) associated with each head.

Shifting means 48 are operatively connected to transfer tip 46 for moving it along axis A, toward and away from its raised position. The shifting means can be, for example, an actuator, such as a z-motion actuator adapted to move the transfer tip in a linear or vertical fashion. In one exemplary arrangement, a solenoid assembly includes a solenoid piston movable between two positions. The lower end of the piston, in this embodiment, is connected to the upper end of the transfer tip. Upon activation, the piston is drawn downwardly (z direction), thereby shifting the transfer tip to its lowered position. Upon release, the piston returns to its normal, raised position, e.g., under spring bias, thereby shifting the transfer tip to its raised position. Many solenoids are available from commercial sources, and suitable models can be readily chosen by those skilled in the art. In one embodiment, the solenoid is operable to shift the transfer tip up and down over a stroke of from about 2 to about 3 cm, and preferably about 2.5 cm.

Other devices, useful as shifting means, include, for example, pneumatic, hydraulic, magnetostrictive, and piezoelectric actuators, as well as motor assemblies (e.g., steppers) operable to generate a downward motive force followed by reciprocation. Several particular assemblies which can be adapted for use herein as the shifting means are disclosed, for example, in U.S. Pat. Nos. 3,164,304; 3,329, 964; 3,334,354; 5,443,791; 5,525,515; 5,551,487; 5,601, 980; and 5,807,522; each of which is expressly incorporated herein by reference.

Positioning means can be utilized to move the transfer tip linearly or in an x-y plane to locate the transfer head at a selected deposition position over the transport pathway. In one exemplary arrangement of the positioning means, the transfer device is carried on a movable arm or support that can be moved to a desired position and then releasably clamped or locked down. Such positioning can be accomplished in a manual or automated fashion, as desired. Both manual and automated positioning arrangements are well known, and suitable arrangements can be readily chosen by those skilled in the art.

Exemplary automated devices useful for positioning include, for example, robots with electronically controlled linked or crossed movable arms, such as a SCARA, gantry and Cartesian robots. In one embodiment, an x-y positioning assembly is employed, comprising a motorized x-y carriage or rail arrangement. In another embodiment, the transfer head is threadedly mounted on a worm screw that can be driven (rotated) in a desired direction by a stepper motor, as directed by the control unit. It is understood, of course, that any other robotic mechanism could be used in accordance with the present invention so long as it can accomplish substantially the same purposes and secure substantially the same result. Several exemplary x-y positioning assemblies which can be readily adapted for use herein as the positioning means are disclosed, for example, in U.S. Pat. Nos. 5,443,791; 5,551,487; and 5,587,522; each of which is expressly incorporated herein by reference.

In an exemplary embodiment of a manually operable positioning assembly, the transfer head attaches to a support adapted to ride along a rail extending laterally or obliquely over the transport pathway. The transfer head can be positioned at a desired location by manually sliding the support along the rail, and then locked down by turning a securing bolt threadedly received in a bore extending through the support, so that the bolt's terminal end pressingly engages the rail. In another embodiment, a manually adjustable x- and/or y-axis lead screw arrangement is employed.

As previously noted, a base, indicated generally as 50, is provided under transport pathway P. Base 50 includes at least one reagent-holding region whereat one or more selected reagents can be placed (such as the region of base 50 below transfer head 44 in FIG. 1). In a typical operation, each reagent-holding region remains stationary (at a fixed position along the base below an associated transfer tip) while one or more substrates are moved thereover along the transport pathway, as by way of conveyor 12.

Further regarding the reagent holding region(s), in one embodiment, one or more reservoirs are provided in the base itself, each suitable for directly receiving and holding a selected reagent. For example, a reservoir in the nature of a well or cup can be integrally formed in, or attached to, a surface of the base confronting the transport pathway. In another embodiment, the base is provided with one or more locating features for removably receiving a reagent-containing reservoir, such as a tube or vial, at a desired position. In the exemplary arrangement of FIGS. 1 through 4, base 50 takes the form of an elongated structure having upper and lower walls, denoted as 52 and 54 (FIG. 2), respectively, joined by opposed, lateral sidewalls 56, 58. The long dimension of base 50 is disposed substantially parallel to the direction of substrate movement along transport pathway P. The four walls (52, 54, 56, 58) of base 50 define an elongated internal cavity or channel, indicated at 63, having a generally rectangular cross-sectional profile, as visible in FIG. 4.

A plurality of apertures, such as 62a–62c shown in FIG. 2, extend through upper wall 52 of base 50 at spaced locations therealong. According to one preferred embodiment, at least one of the apertures in the base is laterally offset from the other apertures. Instead of providing only one aperture at each of the spaced locations along the base, other embodiments provide two or more apertures disposed laterally or obliquely across the base at each location.

Each aperture is configured to receive a reagent-holding reservoir, such as one of tubes 70a–70d. The reservoirs can be held in any suitable manner. For example, as best seen with regard to tube 70d of FIG. 4, each tube can include a circumferential rim 71 about its upper opening. The diameter of tube 70d, measured across rim 71, is greater than the diameter across any one of the apertures in base 50. The region of tube 70d below its rim 71, on the other hand, is configured with a diameter smaller than the diameter of the apertures. By this construction, tube 70d can be inserted, bottom first, into a selected one of the apertures, until the lower side of its rim abuts the region of base 50 circumscribing the aperture. It will be understood that the tube depicted represents but one variety of many types of tubes, or other reservoirs, that can be used, and that other tube configurations can be accommodated in the base with equal effectiveness. For example, a tube of another form may be longer and thereby rest against the bottom wall of base, instead of being supported at its rim. Similarly, the apertures may be sized to accommodate tubes of larger or smaller diameters than the tube shown.

It should be appreciated that any desired type or form of reagent can be held in the various reagent reservoirs (e.g., liquids, slurries, micro-beads, etc.). The reagents in the various reservoirs can all be the same, or they can differ. For example, 1,000 different tubes along the transport pathway can contain, respectively, 1,000 different primer sets for spotting onto one or more substrates for use in primer-initiated polymerase chain reaction (PCR).

The upper wall of the base can be of unitary construction, e.g., an elongated strip of plastic, metal and/or wood; or, alternatively, it can be of a modular design. In a general embodiment of the latter, the upper wall is comprised of a plurality of individual subunits, in the nature of panels or tiles, laid down end-to-end. Each subunit, in this embodiment, includes one or more tube-receiving apertures formed therethrough. One particular embodiment provides numerous sets of panels, with the members of each set being characterized by a particular aperture configuration/pattern. In use, panels suitable for the task at hand are chosen from the various sets and laid down (and, optionally, locked in place) to provide an upper wall having a custom arrangement of apertures therealong. Selected reagent tubes can then be inserted into the various apertures for use in a spotting operation (described below). Between spotting operations, the panels can be dissembled and reassembled, as desired.

In one embodiment, the abutting edges of walls 52, 54, 56, 58 are adjoined in a substantially fluid-tight fashion, permitting the flow of one or more selected fluids (gas and/or liquid) through channel 63. In this regard, one or more flow lines, such as 64 and 65 in FIG. 2, can be connected at one end of base 50, via respective fittings 67, 68. Each flow line, in the illustrated arrangement, is adapted to communicate a selected remote fluid source (not shown) with the channel 63 of base 50. One or more exit ports (not shown) can be provided at the other end of base to allow egression of any fluid(s) passed through the base. As previously described, with the reagent tubes in their seated positions, a substantial portion of each tube (e.g., the region below its upper lip) extends down into channel 63. Accordingly, with the tubes in place, fluid(s) passed through the channel (e.g., a coolant) can contact the accessible exterior surfaces of such reservoirs. With the reservoirs removed, and the transfer tips shifted through the (empty) apertures to their lowered positions, fluid(s) passed through the channel (e.g., a cleaning fluid) can contact the accessible surfaces of such tips. Exemplary operations utilizing such features are described more fully below.

For those embodiments employing a contact-type transfer tip, it may be desirable to utilize means for preventing significant deflection of the belt or web as a result of such contact. For example, one or more shutter mechanisms (not shown) can be provided along the base. In one embodiment, a shutter mechanism occupies a narrow, substantially planar region between the lower surface of the belt or web and the upper regions of the reservoirs, at each of the spaced locations along the base. Such shutter mechanisms are operable, at the direction of the control unit, to intermittently form substantially rigid surfaces for supporting regions of the belt during spotting operations. Particularly, each shutter is open when the transfer tip is shifted through an opening to its lowered position to pick up reagent from a reagent reservoir, and closed when the transfer tip is shifted from its raised position into contact with a substrate for forming a reagent spot thereon. Alternatively, or in addition, the belt or web can be subjected to an increased tension during contact spotting, using conventional belt tensioning assemblies.

The positions of the substrates along the conveyor belt or web can be monitored by any suitable means. In certain embodiments, for example, the position of each substrate is monitored in terms of conveyor travel length increments. In this regard, one preferred embodiment of the invention contemplates the use of a stepper motor mechanically engaged with the conveyor belt or web such that each rotational step of the motor induces movement of the conveyor belt or web a given travel length increment. The control unit is programmed to track the steps of the motor, in accordance with conventional principles, and thereby determine the position of each substrate along the belt. Optionally, the stepper motor control system can include a home switch associated with the motor that will allow the control unit to determine a starting or reference "home" position.

Another embodiment contemplates the use of a servo motor mechanically engaged with the conveyor belt or web such that rotation of the motor's drive shaft through a given angle induces movement of the belt or web a known travel length increment. Here, an encoder monitors the rotation of the motor's shaft and generates a pulse for each chosen increment of shaft rotation. The encoder is electrically connected to the control unit which counts or otherwise tracks the encoder pulses. By monitoring the increments of shaft rotation in this way, corresponding increments of linear travel of the conveyor belt can be readily determined.

Still a further embodiment of position-monitoring means includes a conventional position detector mounted adjacent the conveyor so as to have a field of view directed at the transport pathway. The detector can be, for example, an optic detector, or the like, operable to generate an output signal when a substrate or substrate-support region is positioned underneath the transfer head. The output of the sensor is fed to the input of the control unit.

The control unit of the reagent-transfer apparatus serves to actuate the conveyor motor and shifting means in a sequence designed for automated operation of the apparatus in forming at least one reagent region on one or more substrates. In this regard, the control unit is constructed, according to conventional microprocessor control principles, to provide appropriate signals to the shifting means and conveyor motor, in a given timed sequence and for an appropriate signaling time. The construction of the unit, and the settings that are selected by the user to achieve a desired reagent-spot pattern, will be understood from the following description of a typical apparatus operation.

In one general embodiment of a spotting method according to the present invention, a plurality of spaced, tandemly-arranged substrates are advanced, e.g., by way of a conveyor, along a transport pathway extending over one or more reagent-supply locations, such as reservoirs held in a base. From a position over the reagent-supply location(s) and the pathway, a reagent-transfer instrument, or tip, is extended along an axis through an intervening region separating an adjacent pair of advancing substrates to contact reagent held at the reagent-supply location. The reagent-transfer instrument is then withdrawn, along with a portion of such reagent, through the intervening region to a position above the transport pathway. Next, a selected amount of reagent is transferred from the reagent-transfer instrument onto a selected region or site of a selected substrate or substrate region upstream of the intervening region.

Figure 4:
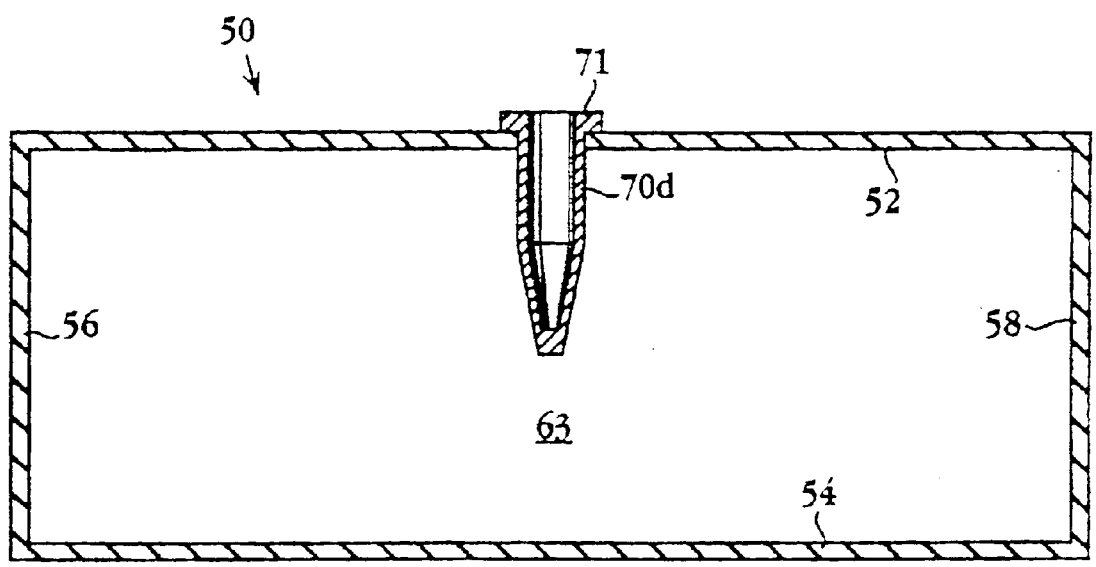
FIG. 4 is a cross-sectional view showing a base portion of the reagent-transfer apparatus of the present invention, as contemplated by one embodiment, with a reagent reservoir seated in an aperture in the upper tall of the base.
Figure 5A:
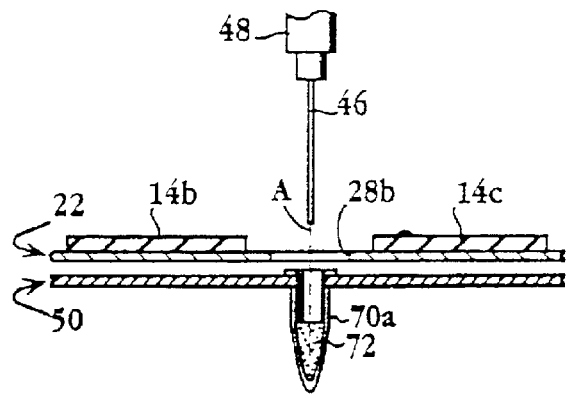
FIGS. 5A–5G depict an exemplary operation wherein a reagent spot is formed on a selected substrate, in accordance with the teachings of the present invention.
Figure 5B:
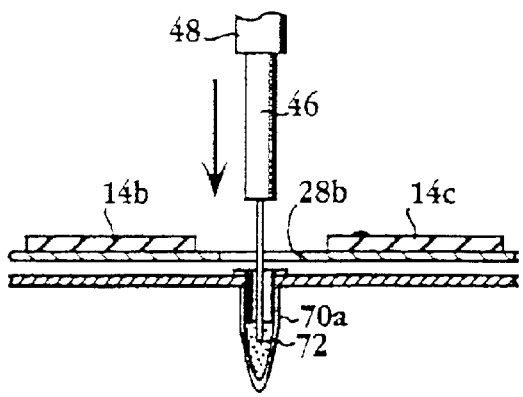
Figure 5C:
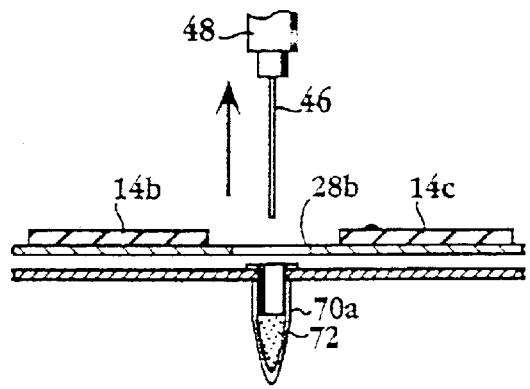
Figure 5D:
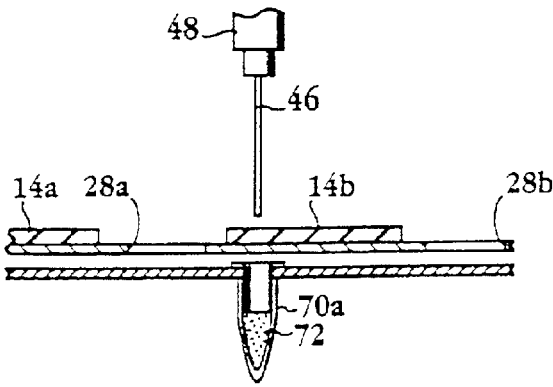
Figure 5E:
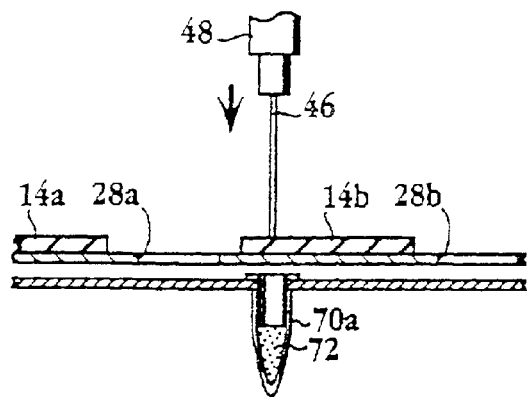
Figure 5F:
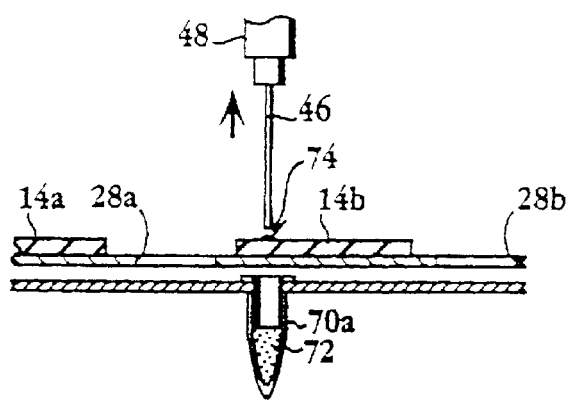
Figure 5G:
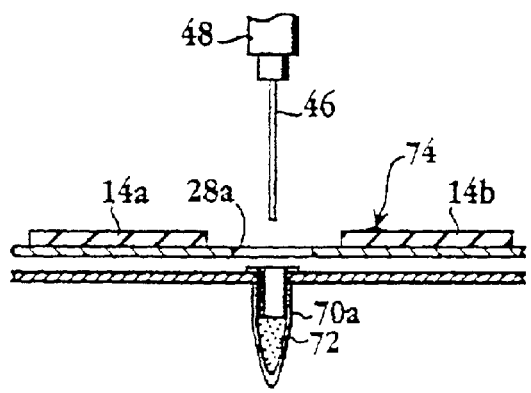

With primary reference to the embodiment of FIGS. 5A through 5G, a typical operation will now be described wherein a reagent spot is placed on a substrate—in this case substrate 14b. The operation is described in connection with an apparatus essentially as depicted in FIGS. 1, 2 and 4. With transfer tip 46 disposed at its raised position, the conveyor motor is signaled to advance belt 22, and any substrates thereon, along the transport pathway (toward the right in the figures) until an open region downstream of the selected substrate 14b, such as opening 28b, becomes positioned under transfer tip 46 (i.e., generally aligned with axis A), at which point the belt is stopped (FIG. 5A). Shifting means 48 is then signaled to shift the transfer tip away from its raised position and through opening 28b to contact a reagent 72 held in base 50 (FIG. 5B). Shifting means 48 then withdraws the tip, along with a portion of such reagent, through the opening to a position above the transport pathway (FIG. 5C). The control unit then signals the conveyor motor to advance belt 22 until a selected region or site of substrate 14b intersects the transfer head's axis A, at which point the belt is again stopped (FIG. 5D). Next, shifting means 48 is signaled to shift the transfer tip away from its raised position toward the selected region of substrate 14b, to transfer a selected amount of reagent, e.g., in the form of a spot 74, from the tip to such region of the substrate (FIGS. 5E and 5F). If desired, the spotting tip can again be shifted, one or more times, to transfer additional reagent to the substrate. Such additional reagent can be placed at the already-laid spots, or, upon incrementally advancing the substrate under the spotting tip, at previously unspotted regions of the substrate. The just-spotted substrate can then be transported downstream (FIG. 5G) for additional spotting at one or more downstream spotting heads, as desired; and the next selected, upstream substrate can be advanced for spotting.

In some cases, it is desired to spot out the reagents in a humid environment so that the droplets do not dry until the arraying operation is complete. For similar reasons, low-volatility solvents are also preferable in such cases.

The just-described operation contemplates an indexed mode of operation, wherein the belt stops and starts repeatedly. It should be appreciated, however, that a continuous mode could be employed instead. If used in the continuous mode, the control unit controls the speed of the conveyor motor, and thus the speed at which substrates are moved along the transport pathway. The control unit also monitors the positions of the various substrates, and signals shifting of the various transfer tips in a fashion permitting reagent retrieval and deposition—without pausing the movement of the belt/substrates.

It should be noted that while only one transfer head is shown in FIG. 1, a device like 44 can be provided at each of the spaced locations along the transport pathway having a reagent reservoir. Each substrate, by this arrangement, can be spotted at one or more of the spaced locations, as desired, during its movement along the transport pathway. Also, in this arrangement, a plurality of spotting operations, such as described above with regard to substrate 14a, can be carried out substantially simultaneously. By providing a spotting head at each of the five reagent-supply locations shown in FIG. 1, for example, a reagent spot can be placed on each of five tandemly-arranged substrates at substantially the same time. The illustrated arrangement can be extended to any desired number of spotting heads. One exemplary embodiment contemplates the use of 1,000 spotting heads disposed sequentially at spaced locations along the transport pathway, at various pre-selected laterally offset positions. By this arrangement, 1,000 spots can be laid per second, or so, with one such spot being placed on each of 1,000 substrates along the transport pathway. In another embodiment, four spotting heads are disposed laterally or obliquely across the transport pathway (along with respective reagent reservoirs thereunder) at each of 250 spaced locations—again, in a selected laterally offset pattern. The various spotting heads at each of the spaced locations can be operated individually, or in mass. Preferably, each transfer tip is independent of all other transfer tips and can therefor be adjusted to accommodate a wide range of spot spacing. This feature reduces tolerance problems associated with conventional transfer devices having fixed spatial relationships. By the above arrangements and methods, a very compact interleaving of reagent spots can be formed on each substrate's surface—the practical density being limited only by the volume of liquid transferred and the wetability or surface feature size of the substrate. Fully arrayed substrates can be pulled off of the conveyor at the end of the transport pathway at a relatively rapid rate (e.g., 1 substrate about every 1 to 2 seconds).

The independent construction of each transfer device, as provided herein, also allows for the service/replacement of each transfer device on an individual basis. As mentioned above, each individual transfer tip can be attached to and detached from the head, without affecting or otherwise disturbing any other transfer tip(s) of the apparatus. Conventional transfer schemes that utilize permanently fixed arrays of transfer devices, on the other hand, are inherently deficient if one member of the array malfunctions. In such conventional assemblies, if one of the devices should require service, repair, or replacement, then the entire array of transfer devices must be disassembled and/or replaced. Moreover, in the latter case, any reagents that cannot be retrieved from such conventional devices must also be discarded and replaced.

Preferably, the shifting motion (stroke) of each transfer tip, as taught herein, is kept to a minimum throughout the transfer operation. That is, at its raised position, the transfer tip clears the uppermost region of a substrate by only a small distance, e.g., less than about 2 mm, and preferably less than about 1 mm. Similarly, at its lowered position, the transfer tip only enters the reagent tube to the extent necessary to pick up a desired amount of reagent. Regarding the latter, reagent levels in each tube can be monitored (e.g., optically detected) or calculated so that the control unit can avoid overextending the various transfer tips. This limited motion saves time and, particularly for liquid reagents, avoids concentration variability associated with evaporation.

With a set of reagent tubes in place along the base, any suitable cooling fluid (e.g., a gas, or water) can be passed through the channel of the base to contact the accessible exterior regions of the reagent reservoirs. This can be useful to discourage evaporative loss of the reagents.

After one or more reagent transfer operations have been carried out, it will sometimes be desired to clean the reagent-transfer tips so that a new, different set of reagents can be utilized without substantial risk of cross-contamination. In one embodiment, the reagent reservoirs (tubes) are removed from the apertures along the base, and the transfer tips are then shifted to their lowered positions—with the reagent-contacting portion of each tip passed through a respective aperture to a location inside the base's channel. A suitable cleaning solvent is then flowed through the channel, thereby cleaning the various transfer tips in a substantially simultaneous fashion. Optionally, after such a cleaning operation, a dry, warm gas can be flowed through the channel to dry the transfer tips.

Preferably, the tubes, or other reagent reservoirs, that are supported in the base for supplying the transfer tips with reagents are also the same containers in which the reagents are stored. For example, prior to a spotting operation, an operator or robot can retrieve one or more vessels containing selected reagents from a storage location (e.g., a file cabinet), then open each vessel and place it at a respective supply location along the base. Once the spotting operation has been completed, the vessel can simply be resealed and returned to its storage location. Thus, each reagent remains in its own vessel throughout storage and use. This is contrasted to most conventional schemes where the reagent vessel must be retrieved and then a portion of its contents transferred to another vessel or reservoir—with still further manipulations at the actual point of use. Not only does the present invention provide for reduced handling of each reagent, saving time, it also offers reduced reagent loss as compared to most conventional deposition systems. As just described, reagents that are deposited onto a substrate are preferably transferred from a storage tube, or other reservoir, directly onto the surface of a substrate without the use intermediate containers or lines. After use, the reagent tube is simply resealed prior to storage. It should be appreciated that intermediate containers typically waste fluid because of residues and films that are unavoidably left behind. For applications requiring expensive reagents, intermediate containers can waste an unacceptable amount of fluid.

Certain embodiments of the present invention contemplate the use of an automated shuttle means (e.g., including robots, conveyors, etc.) for retrieving selected reagents from storage and placing each at an appropriate location along the base. Additionally, the shuttle means can be used to return reagents to their storage locations after use. For example, while one set of reagents is in use, the next set of selected reagents can be retrieved by the shuttle and brought to respective locations along the transport pathway adjacent their points of use. At an appropriate time, the shuttle means can remove the just-used set, place the new set in the base, and return the used set to storage. These steps can be repeated (cycled), preferably under the direction of a programmed computing device, as many times as desired.

It should be appreciated that any desired substrate(s) can be used with the present invention, including slides, cards, plates, trays, chips, membranes, and the like. In one general embodiment, the substrate surface is relatively hydrophilic, i.e., wettable. For example, the surface can have native, bound or covalently attached charged groups. One such surface is a glass surface having an absorbed layer of a polycationic polymer, such as poly-l-tysine. In one embodiment, for example, an aqueous or predominantly aqueous reagent solution or biological sample is spotted onto a slide having a hydrophilic surface. In another embodiment, the substrate surface has or is formed to have a relatively hydrophobic character, i.e., one that causes aqueous medium deposited on the surface to bead. A variety of known hydrophobic polymers, such as polystyrene, polypropylene, or polyethylene have desired hydrophobic properties, as do a variety of lubricant or other hydrophobic films that may be applied to the substrate surface.

Those skilled in the art can now appreciate from the foregoing description that the broad teachings of the present invention can be implemented in a variety of forms. For example, rather than utilizing a single linear belt or web for advancing substrates, as illustrated in the drawings, a plurality of conveyors can be arranged to pass off substrates from one conveyor to the next. In one such arrangement, two or more conveyors are arranged end-to-end, with the various conveyors collectively forming a transport pathway of greater length than any one of them. Also, a non-linear conveyor can be utilized, e.g., a carousel-type arrangement, instead of a linear arrangement as depicted in the drawings. Further, the transport pathway can change direction one or more times during or between spotting operations, e.g., two steps forward, two steps back, four steps forward, two steps back, etc. Therefore, while this invention has been described in connection with particular embodiments and examples thereof, the true scope of the invention should not be so limited. Various changes and modification may be made without departing from the scope of the invention, as defined by the appended claims.

It is claimed:

1. A spotting system, comprising:
   a base including one or more areas adapted to hold one or more reagents;
   a conveyor positioned over said base, said conveyor including a surface defining (i) a plurality of substrate-support areas for holding or containing substrates to be spotted with said one or more reagents, and (ii) a plurality of openings permitting access to said one or more base areas;
   a transfer head which is movable along an axis for obtaining reagents from the base through said openings in the conveyor surface; and
   one or more controllers for controlling the movement of the conveyor and the transfer head.

2. The system of claim 1, wherein an elongate flexible belt defines said conveyor.

3. The system of claim 1, which further includes one or more additional transfer heads disposed at spaced positions along said conveyor.

4. The system of claim 3, wherein at least one of said transfer heads is laterally offset from the other transfer heads.

5. The system of claim 3, wherein a plurality of transfer heads are disposed in a row extending laterally or obliquely across the conveyor surface at one or more of said spaced positions.

6. A reagent-manipulation apparatus, comprising:
   a conveyor including a surface with a plurality of spaced, tandemly-arranged substrate-support regions, each adapted to support a substrate, said conveyor surface defining an opening between each adjacent pair of substrate-support regions;
   a base located under the conveyor and adapted to hold one or more reagents;
   a transfer head being mounted for movement along an axis, between a raised position at which the head is disposed above the conveyor surface and a lowered position whereat the head can contact said one or more reagents; and
   one or more controllers for controlling the movement of the conveyor and transfer head.

7. The system of claim 6, wherein an elongate flexible belt defines said conveyor.

8. The system of claim 6, which further includes one or more additional transfer heads disposed at spaced positions along said conveyor.

9. The system of claim 8, wherein at least one of said transfer heads is laterally offset from the other transfer heads.

10. The system of claim 8, wherein a plurality of transfer heads are disposed in a row extending laterally or obliquely across the conveyor surface at one or more of said spaced positions.

11. A method for accessing a reagent held at a reagent-supply location, under a plurality of spaced substrates, comprising:
    (i) advancing said plurality of spaced substrates along a transport pathway extending over said reagent-supply location; and
    (ii) from a position over said reagent-supply location and said pathway, extending a reagent-transfer instrument through an intervening region separating an adjacent pair of said substrates to contact said reagent held at said reagent-supply location.

* * * * *